US012755567B2

(12) United States Patent
Zeng et al.

(10) Patent No.: US 12,755,567 B2
(45) **Date of Patent: *Oct. 6, 2026**

(54) MACHINE-LEARNING-ENABLED IMPUTATION OF SPATIAL OMICS DATA BASED ON HISTOPATHOLOGY IMAGE DATA

(71) Applicant: Insitro, Inc., South San Francisco, CA (US)

(72) Inventors: Haoyang Zeng, Redwood City, CA (US); Jeevaa Velayutham, Shah Alam (MY); Christopher Probert, Mill Valley, CA (US)

(73) Assignee: Insitro, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/341,997

(22) Filed: Sep. 26, 2025

(65) Prior Publication Data

US 2026/0024360 A1 Jan. 22, 2026

Related U.S. Application Data

(63) Continuation of application No. 18/991,159, filed on Dec. 20, 2024, now Pat. No. 12,450,926, which is a (Continued)

(51) Int. Cl.
*G06V 20/69* (2022.01)
*G06T 5/70* (2024.01)

(Continued)

(52) U.S. Cl.
CPC .............. *G06V 20/695* (2022.01); *G06T 5/70* (2024.01); *G06T 5/73* (2024.01); *G06T 7/0012* (2013.01);

(Continued)

(58) Field of Classification Search
CPC .... G06V 20/695; G06V 10/25; G06V 10/774; G06V 2201/07; G06T 5/70; G06T 5/73;

(Continued)

(56) References Cited

U.S. PATENT DOCUMENTS 9,286,672 B2 3/2016 Madabhushi
2022/0367053 A1 11/2022 Mahmood (Continued)

OTHER PUBLICATIONS

Rahman et al,. A ssim guided cgan architecture for clinically driven generative image synthesis of multiplexed spatial proteomics channels. "(Year: 2023)".

(Continued)

*Primary Examiner* — Wassim Mahrouka
(74) *Attorney, Agent, or Firm* — Weaver Austin Villeneuve & Sampson LLP

(57) ABSTRACT

The present disclosure relates generally to machine learning techniques, and more specifically to machine learning techniques for generating synthetic spatial omics data based on histopathology image data. An exemplary system for generating synthetic spatial omics images comprises: one or more processors; a memory; and one or more programs, wherein the one or more programs are stored in the memory and configured to be executed by the one or more processors, the one or more programs including instructions for: receiving a histopathology image depicting a diseased region of interest of an input tissue sample; and generating a synthetic spatial omics image depicting one or more stained structures of interest within the diseased region of interest by inputting the histopathology image into a generator of a trained generative adversarial network (GAN) model.

19 Claims, 10 Drawing Sheets

Related U.S. Application Data continuation of application No. PCT/US2024/052940, filed on Oct. 25, 2024.

(60) Provisional application No. 63/546,144, filed on Oct. 27, 2023.

(51) Int. Cl.

| | |
|---|---|
| ***G06T 5/73*** | (2024.01) |
| ***G06T 7/00*** | (2017.01) |
| ***G06T 7/33*** | (2017.01) |
| ***G06T 11/00*** | (2026.01) |
| ***G06V 10/25*** | (2022.01) |
| ***G06V 10/774*** | (2022.01) |
| ***G16H 20/00*** | (2018.01) |

(52) U.S. Cl.

CPC ................ *G06T 7/33* (2017.01); *G06T 11/00* (2013.01); *G06V 10/25* (2022.01); *G06V 10/774* (2022.01); *G16H 20/00* (2018.01); *G06T 2207/20081* (2013.01); *G06T 2207/20084* (2013.01); *G06T 2207/30024* (2013.01); *G06V 2201/07* (2022.01)

(58) Field of Classification Search

CPC ......... G06T 7/0012; G06T 7/33; G06T 11/00; G06T 2207/20081; G06T 2207/20084; G06T 2207/30024; G16H 20/00

See application file for complete search history.

(56) References Cited

U.S. PATENT DOCUMENTS

| | | | |
|---|---|---|---|
| 2023/0117405 | A1 | 4/2023 | Verma |
| 2023/0306761 | A1 | 9/2023 | Sirbulescu et al. |
| 2024/0161519 | A1 | 5/2024 | Ho |
| 2024/0194292 | A1 * | 6/2024 | Choi ..................... G06T 7/0012 |
| 2024/0371184 | A1 | 11/2024 | Comiter |

OTHER PUBLICATIONS

International Search Report and Written Opinion received for International Patent Application No. PCT/US204/052940 mailed on Apr. 4, 2025, 12 pages.

Huang et al., (2021) "Machine Learning Applications for Therapeutic Tasks with Genomics Data," Patterns, 2 (10):100328, 29 pages.

Macenko et al., (2009). "A method for normalizing histology slides for quantitative analysis," IEEE International Symposium on Biomedical Imaging: From Nano to Macro, 1107-1110.

* cited by examiner

MACHINE-LEARNING-ENABLED IMPUTATION OF SPATIAL OMICS DATA BASED ON HISTOPATHOLOGY IMAGE DATA

CROSS REFERENCE TO RELATED APPLICATIONS

An Application Data Sheet is filed concurrently with this specification as part of the present application. Each application that the present application claims benefit of or priority to as identified in the concurrently filed Application Data Sheet is incorporated by reference herein in its entirety and for all purposes.

FIELD OF INVENTION

The present disclosure relates generally to machine learning techniques, and more specifically to machine learning techniques for generating synthetic spatial omics data based on histopathology image data.

BACKGROUND

Spatial omics can refer to spatially resolved molecular techniques designed for the analysis of biological molecules in their native location within a tissue sample to maintain the spatial context. Spatial omics technology has emerged as a powerful tool that can characterize the magnitude and the spatial patterns of molecular activity simultaneously, thus enabling more effective ways to dissect tumor microenvironment and understand cell-to-cell interactions in neuronal diseases. Unlike classic omics assays, spatial omics assay can be paired with other spatial readouts such as histopathology image data indexed against the same physical coordinates.

Spatial omics can include spatial proteomics, spatial transcriptomics, spatial epigenetics, etc. Spatial proteomics involves the study of spatial organization of proteins within cells. A spatial proteomics image can depict the spatially resolved abundance of expressed protein across a diseased region of interest. Spatial transcriptomics involves the study of spatial organization of mRNA transcripts within cells. A spatial transcriptomics image can depict the spatially resolved abundance of expressed RNA transcripts. Spatial epigenetics involves the study of spatial organization of epigenetic markers within cells, such as chromatin accessibility or histone modifications. A spatial epigenetic image can depict the spatially resolved level of epigenetic markers. In general, spatial omics arrays can be applied on fixed tissues together with stains commonly-used in clinical practice, such as hematoxylin and cosin (H&E) stain, to allow the integration of morphological data and omics data spatially resolved at the single-cell level.

However, similar to other omics assays such as single-cell RNA-seq techniques, spatial omics data can be expensive and time-consuming to obtain due to the costly equipment and analytics required. Thus, spatial omics data is not widely available for large cohorts of the population and thus cannot be widely used in clinical and discovery settings.

BRIEF SUMMARY

Disclosed herein are exemplary devices, apparatuses, systems, methods, and non-transitory storage media using machine learning techniques to generate synthetic spatial omics image data. Embodiments of the present disclosure include an end-to-end computational pipeline that imputes spatially resolved analyte concentration from histopathology images. The pipeline can obtain tissue slides on which both histology staining (e.g., hematoxylin and cosin (H&E) stain image data, trichrome stain image data, etc.) and a spatial biology assay (e.g., spatial proteomics, spatial transcriptomics, etc.) have been measured to produce high-content image readouts. The pipeline can train a machine learning model (e.g., a generative adversarial network (GAN) model) that is configured to predict the spatial proteomics assay readout from an input histopathology image. After the machine learning model is trained, the pipeline can impute spatially resolved protein abundance for histology images of tissues for which no matched spatial proteomics data was available.

The machine learning model can be trained using a training dataset comprising a histopathology image set and a corresponding spatial omics image set. To obtain the training dataset, the system may first receive a training histopathology image of a training tissue sample and a training spatial omics image of the training tissue sample. Each of the training histopathology image and the training spatial omics image comprises a plurality of identified landmarks (e.g., cell nuclei). The system can register the training histopathology image and the training spatial omics image based on the plurality of landmarks identified in the training histopathology image and the plurality of landmarks identified in the training spatial omics image. Based on the registration of the two images, the system can align a larger image set, extract relevant image portions (e.g., image portions containing aligned landmarks) from the larger image set, generate tiles from the relevant image portions, and/or perform preprocessing on the tiles to generate the training dataset. The resulting training dataset can comprise histopathology tiles and corresponding spatial omics tiles. The machine learning model can then be trained using the training dataset as described herein.

After the machine learning model is trained, it can be run in inference mode on histology datasets associated with a larger cohort such as a standard-of-care cohort for which spatial omics data is not available. The system can input a histopathology image depicting a diseased region of interest of an input tissue sample and generate a synthetic spatial omics image depicting one or more stained structures of interest within the diseased region of interest by inputting the histopathology image into a generator of the GAN model.

The computational pipeline described herein provides a cheap and fast way to computationally impute spatial omics data for a large number of tissue samples from the cheaper and more available histology images. Accordingly, it can be significantly easier, cheaper, and faster to obtain than real spatial omics data, which requires costly equipment and analytics and can be time-consuming.

Further, the GAN model can be trained using data of a smaller cohort (e.g., a research cohort) and then be run in inference mode to generate synthetic spatial omics data for a significantly larger cohort (e.g., standard-of-care cohort). The synthetic spatial omics data can be used in conjunction with other data readily available for the larger cohort (e.g., longitudinal outcome data, drug response data) to power downstream applications and discoveries. For example, the synthetic spatial omics data can be fed to downstream statistical and machine learning modeling to tackle target discovery and improve patient selection using data at an unprecedented scale and precision.

An exemplary system for generating synthetic spatial omics images comprises: one or more processors; a memory; and one or more programs, wherein the one or more programs are stored in the memory and configured to be executed by the one or more processors, the one or more programs including instructions for: receiving a histopathology image depicting a diseased region of interest of an input tissue sample; and generating a synthetic spatial omics image depicting one or more stained structures of interest within the diseased region of interest by inputting the histopathology image into a generator of a trained generative adversarial network (GAN) model, wherein the GAN model is trained by: receiving a training histopathology image of a training tissue sample, wherein the training histopathology image comprises a plurality of identified landmarks; receiving a training spatial omics image of the training tissue sample, wherein the training spatial omics image comprises a plurality of identified landmarks; registering the training histopathology image and the training spatial omics image based on the plurality of landmarks identified in the training histopathology image and the plurality of landmarks identified in the training spatial omics image; generating, based on the registration of the training histopathology image and the training spatial omics image, a training dataset comprising a histopathology image set and a corresponding spatial omics image set; and training the GAN model based on the generated training dataset.

In some embodiments, the histopathology image depicting the diseased region of interest of the input tissue sample comprises a hematoxylin and cosin (H&E) stain image, a trichrome stain image, an immuno-histochemistry (IHC) stain image, or a Fluorescence In Situ Hybridization (FISH) stain image.

In some embodiments, the generated synthetic spatial omics image comprises a synthetic spatial proteomics image, a synthetic spatial transcriptomics image, or a synthetic spatial epigenetic image.

In some embodiments, the one or more stained structures of interest comprise one or more proteins of interest, DNA, autofluorescence of tissues, or any combination thereof.

In some embodiments, the one or more proteins of interest comprise: DAPI, Cy5, TRITC, FOXP3 (D2W8E), Perforin_C, p-STAT3_C, HLA-I (A, B, or C), TGF-beta, GRZMB_A, GFAP_D, LAG-3_B, TMEM119_C, CD45RO_A, PD-1 EPR4877 (2), HLA-DR_B, PD-L1, CD68 PG-M1, CD19_A, NKG2D_B, TIM-3_A, CD20 L26, LCK_B, CD8 4B11, P2RY12_A, CD4 EPR6854, CD11c, CD205_D, CD163, CD31, or any combination thereof.

In some embodiments, the one or more programs further include instructions for: identifying the plurality of landmarks in the training histopathology image by isolating, from the training histopathology image, image data corresponding to the plurality of landmarks by performing color deconvolution.

In some embodiments, the one or more programs further include instructions for: identifying the plurality of landmarks in the training spatial omics image by isolating, from the training spatial omics image, image data corresponding to the plurality of landmarks by selecting a channel from a plurality of channels.

In some embodiments, the plurality of landmarks identified in the training histopathology image or the plurality of landmarks identified in the training spatial omics image comprise: one or more cell nuclei.

In some embodiments, registering the training histopathology image and the training spatial omics image comprising obtaining a transformation function.

In some embodiments, the one or more programs further include instructions for: performing noise removal on the spatial omics image set of the training dataset.

In some embodiments, the generator of the GAN model comprises a convolutional neural network.

In some embodiments, the generator of the GAN model is based on a U-Net model.

In some embodiments, the discriminator of the GAN model comprises a PatchGAN discriminator model.

In some embodiments, the one or more programs further include instructions for: predicting, based on the synthetic spatial omics image, an outcome of a patient associated with the input tissue sample.

In some embodiments, the one or more programs further include instructions for: identifying, based on the synthetic spatial comics image, a treatment for a patient associated with the input tissue sample.

In some embodiments, the one or more programs further include instructions for: identifying, based on the synthetic spatial comics image, a biomarker.

In some embodiments, the one or more programs further include instructions for: identifying, based on the synthetic spatial comics image, one or more spatial motifs.

In some embodiments, the one or more programs further include instructions for: displaying the synthetic spatial omics image as an overlay over the histopathology image of the input tissue sample.

An exemplary method for generating synthetic spatial omics images comprises: receiving a histopathology image depicting a diseased region of interest of an input tissue sample; and generating a synthetic spatial omics image depicting one or more stained structures of interest within the diseased region of interest by inputting the histopathology image into a generator of a trained generative adversarial network (GAN) model, wherein the GAN model is trained by: receiving a training histopathology image of a training tissue sample, wherein the training histopathology image comprises a plurality of identified landmarks; receiving a training spatial omics image of the training tissue sample, wherein the training spatial omics image comprises a plurality of identified landmarks; registering the training histopathology image and the training spatial omics image based on the plurality of landmarks identified in the training histopathology image and the plurality of landmarks identified in the training spatial omics image; generating, based on the registration of the training histopathology image and the training spatial omics image, a training dataset comprising a histopathology image set and a corresponding spatial omics image set; and training the GAN model based on the generated training dataset.

An exemplary non-transitory computer-readable storage medium stores one or more programs for generating synthetic spatial omics images, the one or more programs comprising instructions, which when executed by one or more processors of an electronic device, cause the electronic device to perform: receiving a histopathology image depicting a diseased region of interest of an input tissue sample; and generating a synthetic spatial omics image depicting one or more stained structures of interest within the diseased region of interest by inputting the histopathology image into a generator of a trained generative adversarial network (GAN) model, wherein the GAN model is trained by: receiving a training histopathology image of a training tissue sample, wherein the training histopathology image comprises a plurality of identified landmarks; receiving a training spatial omics image of the training tissue sample, wherein the training spatial omics image comprises a plurality of identified landmarks; registering the training histopathology image and the training spatial omics image based on the plurality of landmarks identified in the training histopathology image and the plurality of landmarks identified in the training spatial omics image; generating, based on the registration of the training histopathology image and the training spatial omics image, a training dataset comprising a histopathology image set and a corresponding spatial omics image set; and training the GAN model based on the generated training dataset.

DETAILED DESCRIPTION

Figure 1:
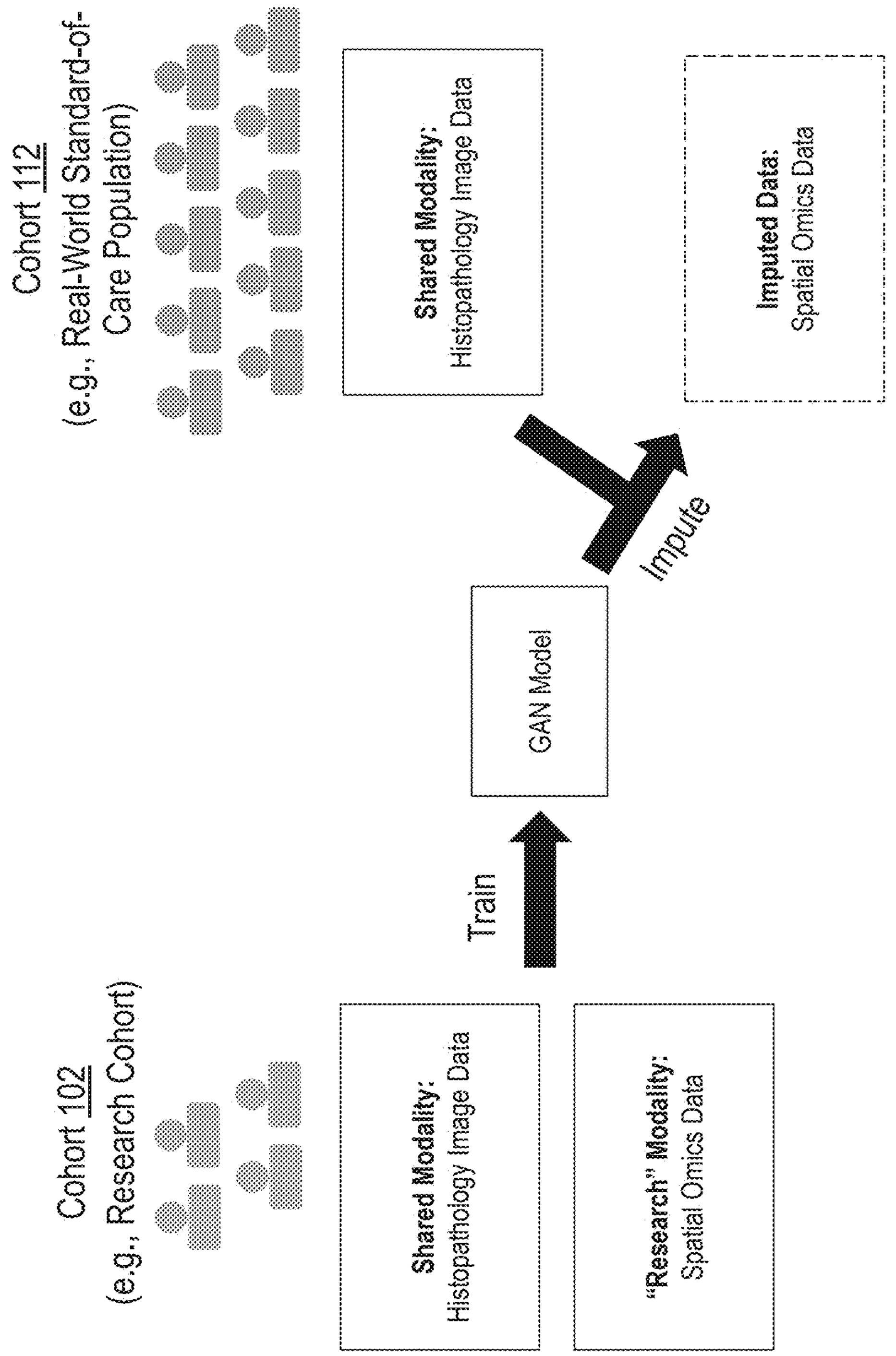
FIG. 1 illustrates an exemplary platform for leveraging machine learning techniques to bridge the gap between research biological data and real-world biological data, in accordance with some embodiments.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

Disclosed herein are exemplary devices, apparatuses, systems, methods, and non-transitory storage media using machine learning techniques to generate synthetic spatial omics image data. Embodiments of the present disclosure include an end-to-end computational pipeline that imputes spatially resolved analyte concentration from histopathology images. The pipeline can obtain tissue slides on which both histology staining (e.g., hematoxylin and eosin (H&E) stain image data, trichrome stain image data, etc.) and a spatial biology assay (e.g., spatial proteomics, spatial transcriptomics, etc.) have been measured to produce high-content image readouts. The pipeline can train a machine learning model (e.g., a generative adversarial network (GAN) model) that is configured to predict the spatial proteomics assay readout from an input histopathology image. After the machine learning model is trained, the pipeline can impute spatially resolved protein abundance for histology images of tissues for which no matched spatial proteomics data was available.

The machine learning model can be trained using a training dataset comprising a histopathology image set and a corresponding spatial omics image set. To obtain the training dataset, the system may first receive a training histopathology image of a training tissue sample and a training spatial omics image of the training tissue sample. Each of the training histopathology image and the training spatial omics image comprises a plurality of identified landmarks (e.g., cell nuclei). The system can register the training histopathology image and the training spatial omics image based on the plurality of landmarks identified in the training histopathology image and the plurality of landmarks identified in the training spatial omics image. Based on the registration of the two images, the system can align a larger image set, extract relevant image portions (e.g., image portions containing aligned landmarks) from the larger image set, generate tiles from the relevant image portions, and/or perform preprocessing on the tiles to generate the training dataset. The resulting training dataset can comprise histopathology tiles and corresponding spatial omics tiles. The machine learning model can then be trained using the training dataset as described herein.

After the machine learning model is trained, it can be run in inference mode on histology datasets associated with a larger cohort such as a standard-of-care cohort for which spatial omics data is not available. The system can input a histopathology image depicting a diseased region of interest of an input tissue sample and generate a synthetic spatial omics image depicting one or more stained structures of interest within the diseased region of interest by inputting the histopathology image into a generator of the GAN model.

The computational pipeline described herein provides a cheap and fast way to computationally impute spatial omics data for a large number of tissue samples from the cheaper and more available histology images. Accordingly, it can be significantly easier, cheaper, and faster to obtain than real spatial omics data, which requires costly equipment and analytics and can be time-consuming.

Further, the GAN model can be trained using data of a smaller cohort (e.g., a research cohort) and then be run in inference mode to generate synthetic spatial omics data for a significantly larger cohort (e.g., standard-of-care cohort). The synthetic spatial omics data can be used in conjunction with other data readily available for the larger cohort (e.g., longitudinal outcome data, drug response data) to power downstream applications and discoveries. For example, the synthetic spatial omics data can be fed to downstream statistical and machine learning modeling to tackle target discovery and improve patient selection using data at an unprecedented scale and precision.

The following description sets forth exemplary methods, parameters, and the like. It should be recognized, however, that such description is not intended as a limitation on the scope of the present disclosure but is instead provided as a description of exemplary embodiments.

Although the following description uses terms "first," "second," etc. to describe various elements, these elements should not be limited by the terms. These terms are only used to distinguish one element from another. For example, a first graphical representation could be termed a second graphical representation, and, similarly, a second graphical representation could be termed a first graphical representation, without departing from the scope of the various described embodiments. The first graphical representation and the second graphical representation are both graphical representations, but they are not the same graphical representation.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

FIG. 1 illustrates an exemplary platform for leveraging machine learning techniques to bridge the gap between research biological data and real-world biological data, in accordance with some embodiments. FIG. 1 depicts two groups of subjects or patients: a cohort 102 and a cohort 112. Cohort 102 may be a relatively small cohort that is organized to collect rich biological information that may require dedicated equipment and setups, often for research purposes. In contrast, cohort 112 may be a larger group of patients for whom data is collected in real-world standard-of-care (SoC) settings. For example, cohort 112 may include data collected from patients as part of receiving medical care and treatments. As discussed below, the data collected for cohort 102 and the data collected for cohort 112 may have shared modalities, but also differ in many aspects.

With reference to FIG. 1, the data collected for cohort 102 and the data collected for cohort 112 may have one or more shared modalities. A shared modality refers to a type of data collected both for cohort 102 (e.g., for research purposes) and cohort 112 (e.g., as part of the SoC). For example, a shared modality may include histopathology image data. A histopathology image can include an image of a tissue sample (e.g., a biopsy or surgical specimen) that is processed and fixed onto slides (e.g., glass slides). To visualize different components of the tissue sample, the tissue may be dyed using one or more stains. The histopathology image can provide insight into a disease and its effect on tissues because the preparation process preserves the morphological structures and characteristics of the tissue sample.

In some embodiments, the histopathology image comprises a hematoxylin and eosin (H&E) stain image, a trichrome stain image, an immuno-histochemistry (IHC) stain image using one or more antibodies, a Fluorescence In Situ Hybridization (FISH) stain image using one or more DNA or RNA probes. The histopathology image may be acquired for both cohort 102 in routine clinical care and cohort 112 in research settings.

The data collected for cohort 102 and the data collected for cohort 112 also differ in many aspects. For example, the data collected for cohort 102 (e.g., a research cohort) may include rich, high-dimensional molecular content that may require dedicated equipment and setups, such as high-content assays. For example, the data may comprise spatial omics data. A spatial omics image provides information about biological molecules in their native location within a tissue sample to maintain the spatial context. In some embodiments, the spatial omics image comprises a spatial proteomics image, which can depict the spatially resolved abundance of expressed protein across the diseased region of interest. In some embodiments, the spatial omics image comprises a spatial transcriptomics image, which can depict the spatially resolved abundance of expressed RNA transcripts. In some embodiments, the spatial omics image comprises a spatial epigenetic image, which can depict the spatially resolved level of chromatin accessibility.

However, the data collected for cohort 102 may be smaller in scale and thus insufficient to power robust biomarker discovery. The data collected for cohort 102 may lack clinical outcome data altogether. Spatial omics data is only available in limited-scale research datasets. In other words, spatial omics data is not collected for cohort 112 as part of the SoC. Thus, spatial omics is collected on a smaller scale and may lack representations from a variety of diseases.

In contrast, the data collected for cohort 112 is larger-scale, often with longitudinal observations, because it is collected as part of the SoC. In some embodiments, the data collected for cohort 112 can include imaging data and outcome data (e.g., mortality, disease diagnosis, disease progression, disease prognosis, disease risk, or any combination thereof, and patient stratification is based on one or more of mortality, disease diagnosis, disease progression, disease prognosis, disease risk, etc.).

Embodiments of the present disclosure can bridge the gap between richly profiled but small-scale research cohorts (e.g., cohort 102 in FIG. 1) and larger-scale real-world patients (e.g., cohort 112 in FIG. 1) for whom data is collected as part of the SoC, allowing discovery of novel clinical insights using SoC data despite its missingness. To do so, the system leverages the shared data modalities between the two cohorts, such as histopathology data (e.g., from H&E or Trichrome biopsy samples), which are data types collected for both cohorts. First, the system can train a machine learning model (e.g., a GAN model) that is configured to receive input data of a shared modality and output imputed or synthetic spatial omics data. Once trained, the machine learning model can be used to obtain imputed spatial omics data for the larger SoC cohort, for which spatial omics data was never collected. Accordingly, the machine learning model allows imputation of one or more research modalities from SoC modalities at scale. The imputed activity data, coupled with the original data collected for the SoC cohort (e.g., longitudinal clinical outcome data), can be used to uncover novel clinical insights as described herein.

Figure 2:
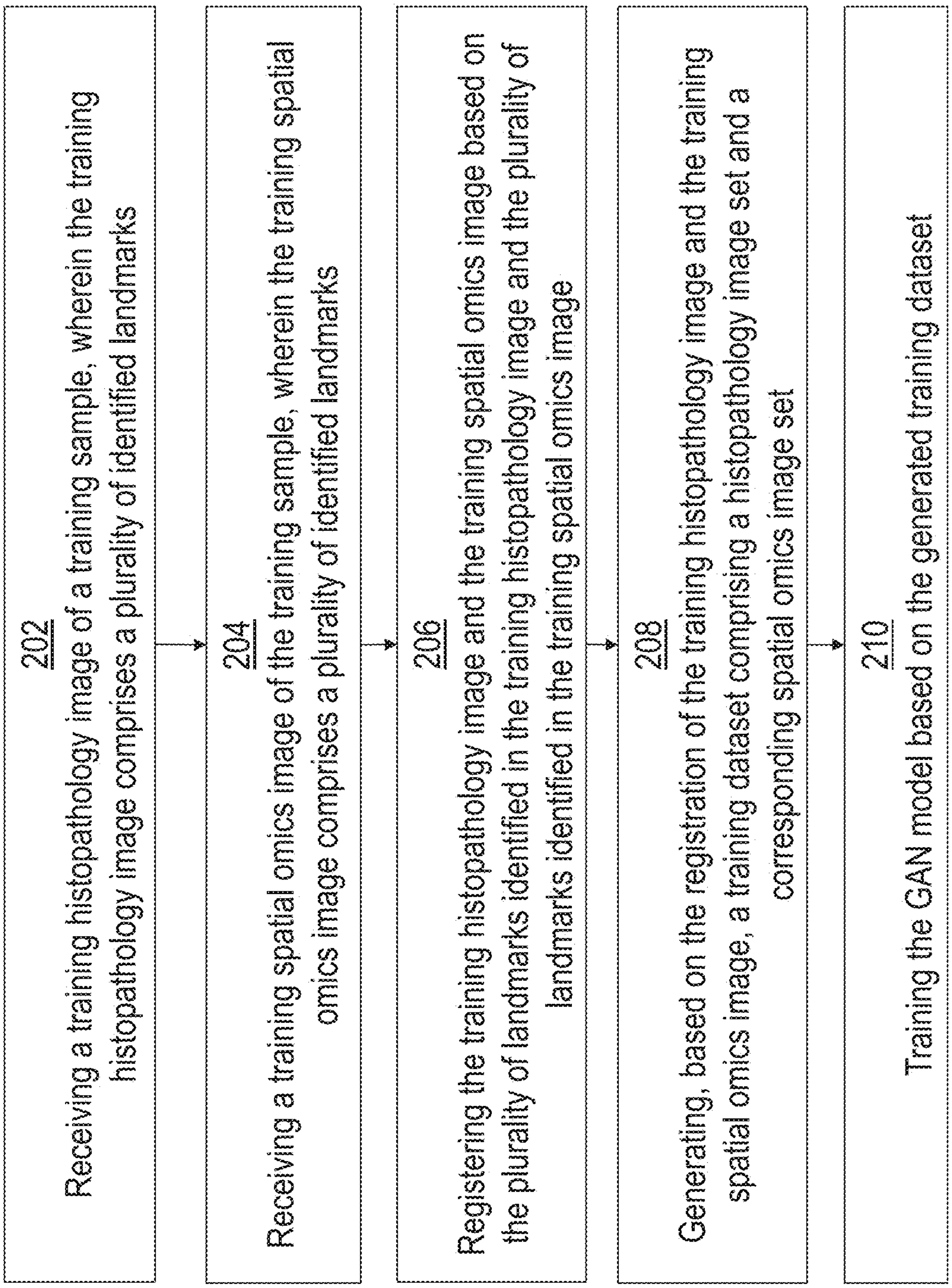
FIG. 2 illustrates an exemplary process for training a machine learning model to generate synthetic spatial omics images, according to some embodiments.

FIG. 2 illustrates an exemplary process 200 for training a machine learning model to generate synthetic spatial omics images, according to some embodiments. Process 200 is performed, for example, using one or more electronic devices implementing a software platform. In some examples, process 200 is performed using a client-server system, and the steps of process 200 are divided up in any manner between the server and one or more client devices. In other examples, process 200 is performed using only a client device or only multiple client devices. In process 200, some steps are, optionally, combined, the order of some steps is, optionally, changed, and some steps are, optionally, omitted. In some examples, additional steps may be performed in combination with the process 200. Accordingly, the operations as illustrated (and described in greater detail below) are exemplary by nature and, as such, should not be viewed as limiting.

At block 202, the system receives a training histopathology image of a training tissue sample. A histopathology image can include an image of a tissue sample (e.g., a biopsy or surgical specimen) that is processed and fixed onto slides (e.g., glass slides). To visualize different components of the tissue sample, the tissue may be dyed using one or more stains. The histopathology image can provide insight into a disease and its effect on tissues because the preparation process preserves the morphological structures and characteristics of the tissue sample. In some embodiments, the histopathology image comprises a hematoxylin and eosin (H&E) stain image, a trichrome stain image, an immunohistochemistry (IHC) stain image using one or more antibodies, a Fluorescence In Situ Hybridization (FISH) stain image using one or more DNA or RNA probes. The histopathology image may be acquired in routine clinical care, as described herein.

As described herein, a training histopathology image is a histopathology image used for the purpose of training a machine learning model (e.g., in block 210 of the process 200). The training histopathology image is not a synthetic image (i.e., an image that is artificially generated by a machine learning model), but rather is a real image of a tissue sample that is captured by a camera. The tissue sample that is depicted in the training histopathology image is referred to as a training tissue sample.

The training histopathology image comprises a plurality of identified landmarks.

Landmarks are visual features (e.g., points, edges, shapes) in an image that can be used to register the image with another image containing the same visual features, as described herein. The plurality of identified landmarks in the training histopathology image can comprise, for example, one or more cell nuclei. To identify the plurality of landmarks in the training histopathology image, the system may perform color deconvolution to isolate, from the training histopathology image, image data corresponding to the plurality of landmarks. In some embodiments, the system performs color deconvolution on the training histopathology image, for example, by performing singular value decomposition (SVD) to isolate the staining effect of hematoxylin, which mainly stains the nucleus of a cell, and then identify the location of the one or more cell nuclei in the image data corresponding to estimated hematoxylin staining training in the training histopathology image accordingly. Additional details related to SVD can be found, for example, in M. Macenko et al., *A method for normalizing histology slides for quantitative analysis,* 2009 IEEE International Symposium on Biomedical Imaging: From Nano to Macro, Boston, MA, USA, 2009, pp. 1107-1110, doi: 10.1109/ISBI.2009.5193250, https://www.cs.unc.edu/~mn/sites/default/files/macenko2009.pdf. The identification of the cell nuclei in the image data corresponding to estimated hematoxylin staining of the training histopathology image can performed via any object recognition techniques, such as scale-invariant feature transform (SIFT).

At block 204, the system receives a training spatial omics image of the training tissue sample. A spatial omics image provides information about biological molecules in their native location within a tissue sample to maintain the spatial context. In some embodiments, the spatial omics image comprises a spatial proteomics image, which can depict the spatially resolved abundance of expressed protein across the diseased region of interest. The spatial proteomics image as described herein may be different from sequencing-based or bead-based spatial proteomics data which are at a lower spatial resolution and measure the average protein expression of all cells in each of the capture spots that are typically greater than 10 uM-radius each. In some embodiments, the spatial omics image comprises a spatial transcriptomics image, which can depict the spatially resolved abundance of expressed RNA transcripts. In some embodiments, the spatial omics image comprises a spatial epigenetic image, which can depict the spatially resolved level of chromatin accessibility.

In some embodiments, the one or more stained structures of interest in the spatial omics image comprise one or more proteins of interest such as cell surface proteins, DNA, and autofluorescence of tissues. In some embodiments, the one or more proteins of interest can comprise: DAPI, Cy5, TRITC, FOXP3 (D2W8E), Perforin_C, p-STAT3_C, HLA-I (A, B, or C), TGF-beta, GRZMB_A, GFAP_D, LAG-3_B, TMEM119_C, CD45RO_A, PD-1 EPR4877 (2), HLA-DR_B, PD-L1, CD68 PG-M1, CD19_A, NKG2D_B, TIM-3_A, CD20 L26, LCK_B, CD8 4B11, P2RY12_A, CD4 EPR6854, CD11c, CD205_D, CD163, CD31, or any combination thereof.

As described herein, a training spatial omics image is a spatial omics image used for the purpose of training a machine learning model (e.g., in block 210 of the process 200). The training spatial omics image is not a synthetic image (i.e., an image that is artificially generated by a machine learning model). The training spatial omics image received in block 204 and the training histopathology image received in block 202 corresponds to the same tissue sample (i.e., the training tissue sample). The training spatial omics image comprises a plurality of identified landmarks. As described above, landmarks are visual features (e.g., points, edges, shapes) in an image that can be used to register the image with another image containing the same visual features. The plurality of identified landmarks in the training spatial omics image can comprise, for example, one or more cell nuclei, and may be the same or overlap with the plurality of identified landmarks in the training histopathology image.

To identify the plurality of landmarks in the training spatial omics image, the system may isolate, from the training spatial omics image, image data corresponding to the plurality of landmarks by selecting a channel from a plurality of channels. In some embodiments, the system can select the DAPI channel, which stains the nucleus, and then identify the location of the one or more cell nuclei in the DAPI channel of the training spatial omics image accordingly. The identification of the cell nuclei in the DAPI channel of the training spatial omics image can performed via any object recognition techniques, such as SIFT techniques.

At block 206, the system registers the training histopathology image and the training spatial omics image based on the plurality of landmarks identified in the training histopathology image and the plurality of landmarks identified in the training spatial omics image. Image registration involves spatially aligning two or more image datasets of the same scene (e.g., tissue sample). Specifically, the system can align the training histopathology image and the training spatial omics image to the same spatial coordinate system. In some embodiments, the system first matches the landmarks identified in the training histopathology image and the landmarks identified in the training spatial omics image. The matching of the landmarks can be performed using, for example, fast approximate nearest neighbor searches (e.g., using the FLANN library). Based on the matched landmarks, the system can identify an image transformation that converts locations (e.g., landmarks) in hematoxylin staining to locations (e.g., landmarks) in the DAPI channel. In some embodiments, the image transformation is obtained using the MAGSAC algorithm.

In some embodiments, the training histopathology image is a portion of a full histopathology slide image. After the transformation function is obtained based on the training histopathology image, the system can apply the transformation function to align the full histopathology slide image with the spatial omics data. The system can identify image portions in the full histopathology image that have landmarks (e.g., cell nuclei) matched to the spatial omics data and crop out only those image portions for subsequent processing (e.g., further alignment, training the machine learning model).

As an example, the system may determine that the spatial omics image is matched to a rotated version of a particular portion of the training histopathology image (e.g., via one or more cell nuclei). Accordingly, the system can determine a transformation function (e.g., a rotation transformation function) to the full histopathology slide image and crop out the matched area(s).

In some embodiments, the identification of landmarks and the registration step can be performed multiple times. For example, the histopathology image portions that have landmarks matched to the spatial omics data, along with the matched spatial omics data, are processed to identify landmarks and aligned again to obtain an improved image transformation function. The first iteration may produce coarsely matched data with a similar field of view, and the additional iteration(s) can be performed to ensure complete alignment at the cell level. The multiple iterations can result in data that captures global structure but also fine grain local alignment, overcoming skew/shift/distortion in the tissue between stains.

At block 212, the system generates, based on the registration of the training histopathology image and the training spatial omics image, a training dataset comprising a histopathology image set and a corresponding spatial omics image set. In blocks 202-206, the system can obtain a plurality of histopathology image portions and a plurality of matched spatial omics image portions. The plurality of histopathology image portions can form the histopathology image set of the training dataset, and the plurality of matched spatial omics image portions can form the corresponding spatial omics image set of the training dataset. In some embodiments, the system can preprocess the spatial omics image set to remove noise and improve imputation quality. Noise removal can include autofluorescence removal or correction, non-specific binding reduction or correction, quantile normalization, inverse hyperbolic sine transformation, scaling, or any combination thereof. In some embodiments, the system can generate paired tiles (e.g., 256 pixels by 256 pixels) for efficient downstream model training.

At block 214, the system trains the GAN model based on the generated training dataset. The GAN model comprises a generator and a discriminator. The generator is configured to receive an input histopathology image and output a synthetic spatial omics image that is as close to a real spatial omics image corresponding to the input histopathology image as possible. In some embodiments, the generator comprises a convolutional neural network (e.g., a U-Net model). The discriminator is configured to receive an input spatial omics image and output a classification of whether the input spatial omics image is real (e.g., sampled from real data) or synthetic (e.g., generated by the generator). In some embodiments, the discriminator comprises a PatchGAN discriminator model. In some embodiments, the GAN model is a conditional GAN model.

In some embodiments, the training of the GAN model can proceed in alternating periods. In a first step, the discriminator trains for one or more epochs. In a second step, the generator then trains for one or more epochs. The two steps can then be repeated to continue to train the generator and the discriminator. The generator can be kept constant during the discriminator training phase. Similarly, the discriminator can be kept constant during the generator training phase. By training both the generator and the discriminator iteratively, the generator can be trained to produce synthetic spatial omics images indistinguishable to real spatial omics images.

Figure 3:
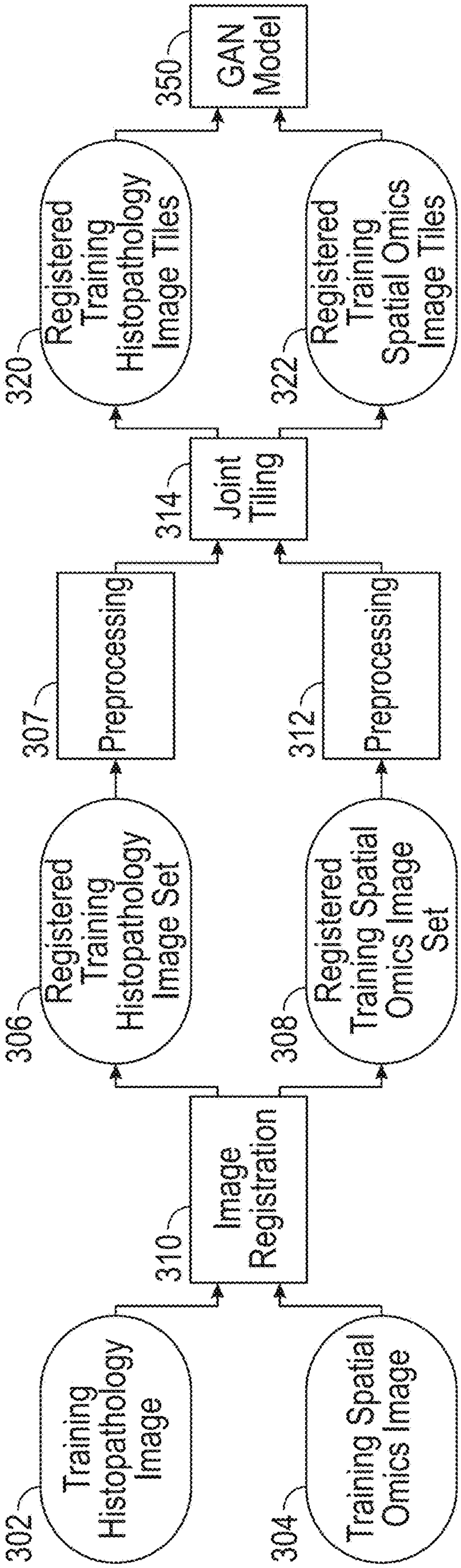
FIG. 3 illustrates an exemplary process for generating a training dataset for training a GAN model, in accordance with some embodiments.

FIG. 3 illustrates an exemplary process 300 for generating a training dataset for training a GAN model, in accordance with some embodiments. The process 300 may correspond to blocks 202-208 of the process 200 in FIG. 2. With reference to FIG. 3, an exemplary system (e.g., one or more electronic devices) receives a training histopathology image 302 of a training tissue sample and a training spatial omics image of the training tissue sample 304. The training histopathology image 302 can comprise a plurality of identified landmarks such as cell nuclei. Similarly, the training spatial omics image 304 can comprise a plurality of identified landmarks. At block 310, the system registers the training histopathology image 302 and the training spatial omics image 304 based on the plurality of landmarks identified in the training histopathology image 302 and the plurality of landmarks identified in the training spatial omics image 304 to obtain a transformation function. The transformation function can be then applied to a larger dataset to obtain a registered histopathology image set 306 and a registered spatial omics image set 308 aligned to the registered histopathology image set 308. At block 307, the system can preprocess the registered histology image set 306 to perform stain correction, remove noise, and improve imputation quality. Stain correction can be done, for example, using the approach described in Macenko et al. At block 312, the system can preprocess the registered spatial omics image set 308 to remove noise and improve imputation quality. Noise removal can include autofluorescence removal or correction, non-specific binding reduction or correction, quantile normalization, inverse hyperbolic sine transformation, scaling, or any combination thereof. At block 314, the system performs joint tiling to generate paired tiles (e.g., 256 pixels by 256 pixels) 320 and 322, which are provided to the GAN model 350 for efficient downstream model training of the GAN model 350.

Figure 4:
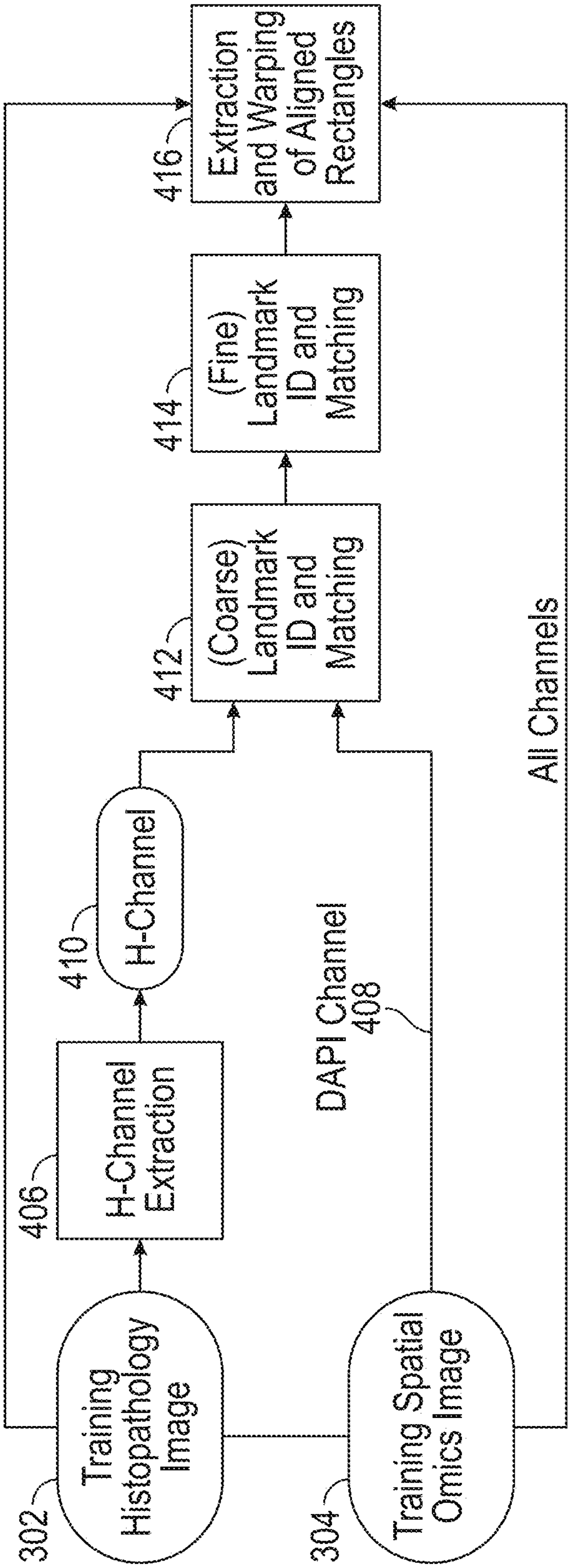
FIG. 4 illustrates an exemplary process for aligning a training histopathology image and a training spatial omics image, in accordance with some embodiments.

FIG. 4 illustrates an exemplary process 400 for aligning a training histopathology image and a training spatial omics image, in accordance with some embodiments. The process 400 may correspond to block 310 of the process 300 in FIG. 3. With reference to FIG. 4, the system receives the training histopathology image 302 of the training tissue sample and the training spatial omics image 304 of the training tissue sample. At block 406, the system can perform color deconvolution (e.g., H-channel extraction) to isolate the staining effect of hematoxylin, which mainly stains the nucleus of a cell. At step 408, the system may isolate, from the training spatial omics image 304, the DAPI channel, which stains the nucleus of a cell.

At block 412, the system can identify the location of the one or more cell nuclei in the image data corresponding to estimated hematoxylin staining in the training histopathology image 302. The identification of the cell nuclei in the image data corresponding to estimated hematoxylin staining of the training histopathology image can performed via any object recognition techniques, such as scale-invariant feature transform (SIFT). The system can also identify the location of the one or more cell nuclei in the DAPI channel of the training spatial omics image 304. The identification of the cell nuclei in the DAPI channel of the training spatial omics image can performed via any object recognition techniques, such as SIFT techniques. The system can further match the identified cell nuclei in the training histopathology image 302 and the identified cell nuclei in the training spatial omics image 304. The matching of the cell nuclei can be performed using, for example, fast approximate nearest neighbor searches (e.g., using the FLANN library). Based on the matched cell nuclei, the system can identify an image transformation that converts locations (e.g., landmarks) in hematoxylin staining to locations (e.g., landmarks) in the DAPI channel. In some embodiments, the image transformation is obtained using the MAGSAC algorithm.

At block 414, the identification and matching of cell nuclei can be performed again. Block 412 may produce coarsely matched data with a similar field of view, and block 414 can be performed to ensure complete alignment at the cell level. The multiple iterations can result in data that captures global structure but also fine grain local alignment, overcoming skew/shift/distortion in the tissue between stains.

At block 416, the system can perform extraction and warping of aligned rectangles. Specifically, the training histopathology image 302 may be a portion of a full histopathology slide image. After the transformation function is obtained based on the training histopathology image 302 in block 416, the system can apply the transformation function to align the full histopathology slide image with the spatial omics data. The system can identify image portions in the full histopathology image that have landmarks (e.g., cell nuclei) matched to the spatial omics data and extract only those image portions for subsequent processing.

Figure 5A:
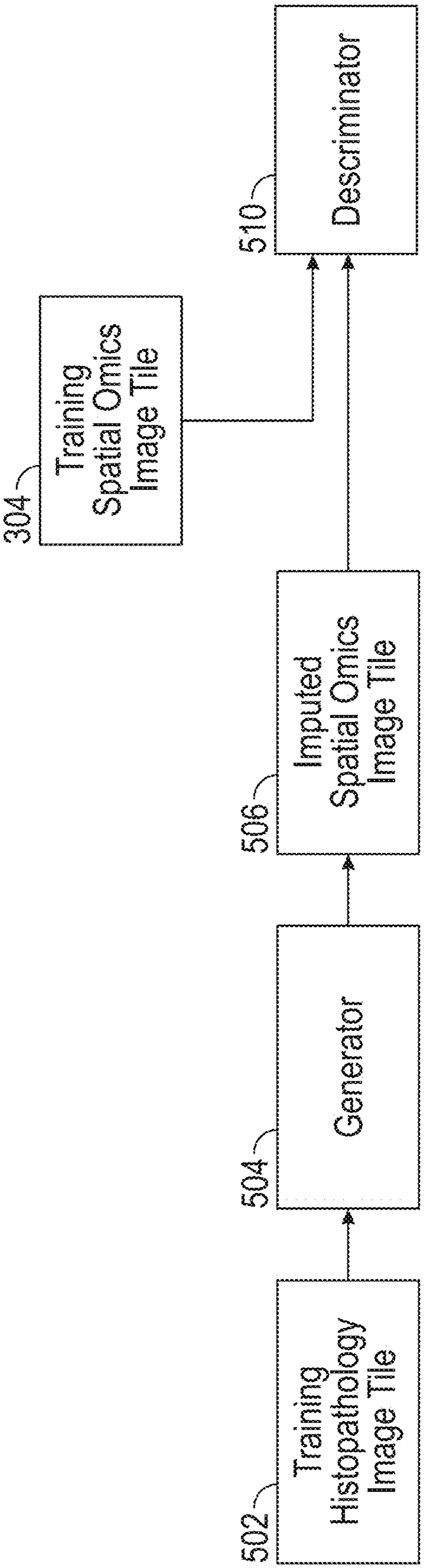
FIG. 5A illustrates an exemplary process for training a GAN model, in accordance with some embodiments.

FIG. 5A illustrates an exemplary process 500 for training a GAN model, in accordance with some embodiments. The GAN model comprises a generator 504 and a discriminator 510. The generator 504 is configured to receive a training histopathology image tile 502 (e.g., from block 320 in FIG. 3) and output a synthetic spatial omics image tile 506. In some embodiments, the generator 504 comprises a convolutional neural network (e.g., a U-Net model). The discriminator 510 is configured to receive a spatial omics image tile, which may be a real spatial omics image tile 508 (e.g., from block 322 in FIG. 3) or the synthetic spatial omics image tile 506, and output a classification of whether it is real (e.g., sampled from real data) or synthetic (e.g., generated by the generator). In some embodiments, the discriminator comprises a PatchGAN discriminator model. In some embodiments, the GAN model is a conditional GAN model.

The discriminator 510 is trained to decrease the error in classifying synthetic and real spatial omics data. The generator 504 is trained to reduce the reconstruction error comparing synthetic and measured spatial omics data and increase the error of discriminator 510. In other words, the training is performed in an adversarial manner. The training of the GAN model can proceed in alternating periods. In a first step, the discriminator trains for one or more epochs. In a second step, the generator then trains for one or more epochs. The two steps can then be repeated to continue to train the generator and the discriminator. The generator can be kept constant during the discriminator training phase. Similarly, the discriminator can be kept constant during the generator training phase. By training both the generator and the discriminator iteratively, the generator can be trained to produces synthetic spatial omics images indistinguishable to real spatial omics images.

In some embodiments, to increase the stability of the training, the system can use a Wasserstein GAN with gradient penalty (WGAN-GP) for the adversarial training process. In the classic setting, binary cross entropy is used in the discriminator and it can make the training unstable. By using Wasserstein loss along with gradient penalty loss, the adversarial training may be more stable. In some embodiments, the system runs the forward/backward pass on discriminator N times (e.g., N=3) before running one forward/backward pass for generator optimization. Further, to improve the quality of the generated images, the system adds structural similarity loss (SSIM loss) to the generator loss along with L1 reconstruction loss. In some embodiments, the GAN model is trained via progressive GAN training techniques.

Figure 5B:
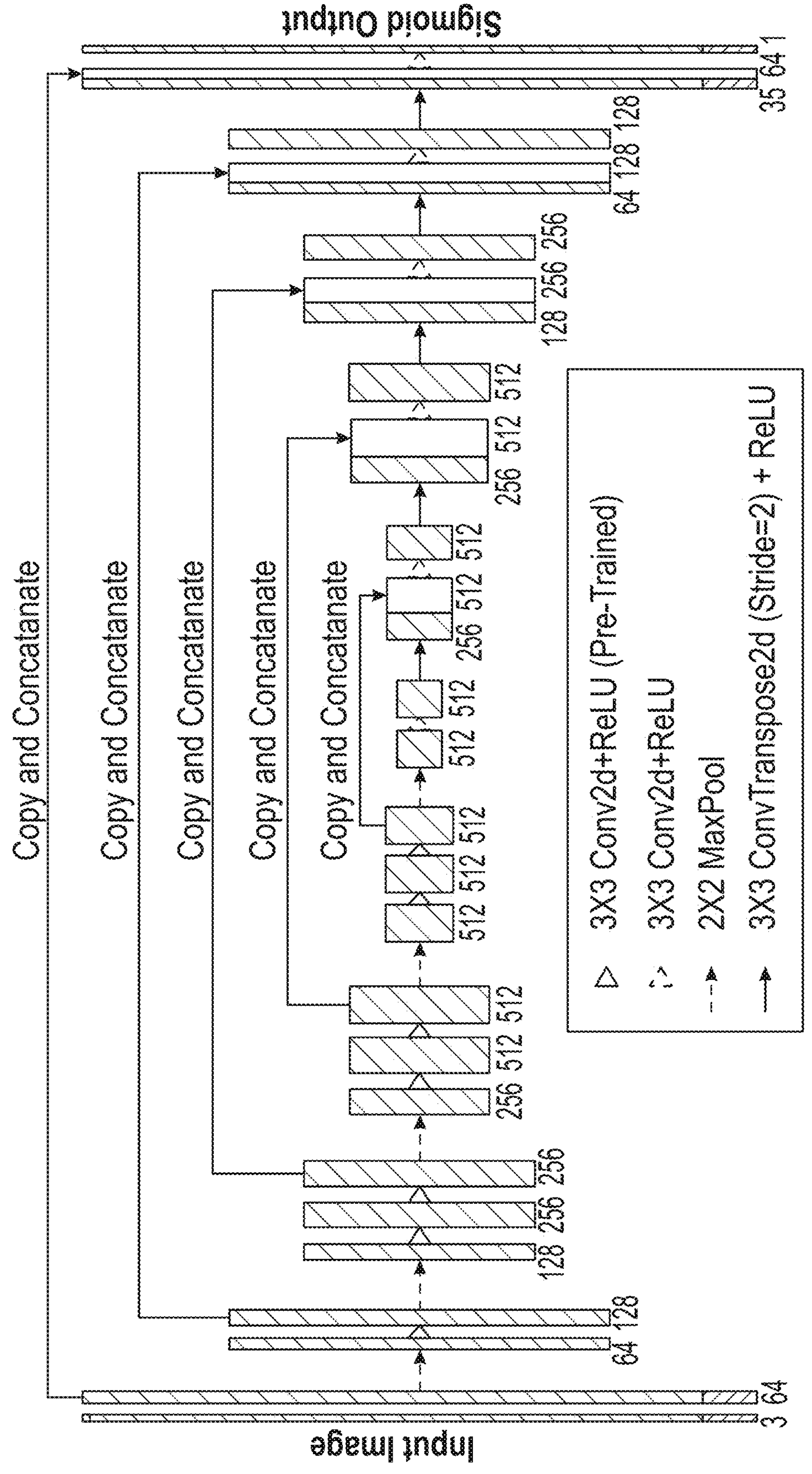
FIG. 5B illustrates an exemplary generator of a GAN model, in accordance with some embodiments.
Figure 5C:
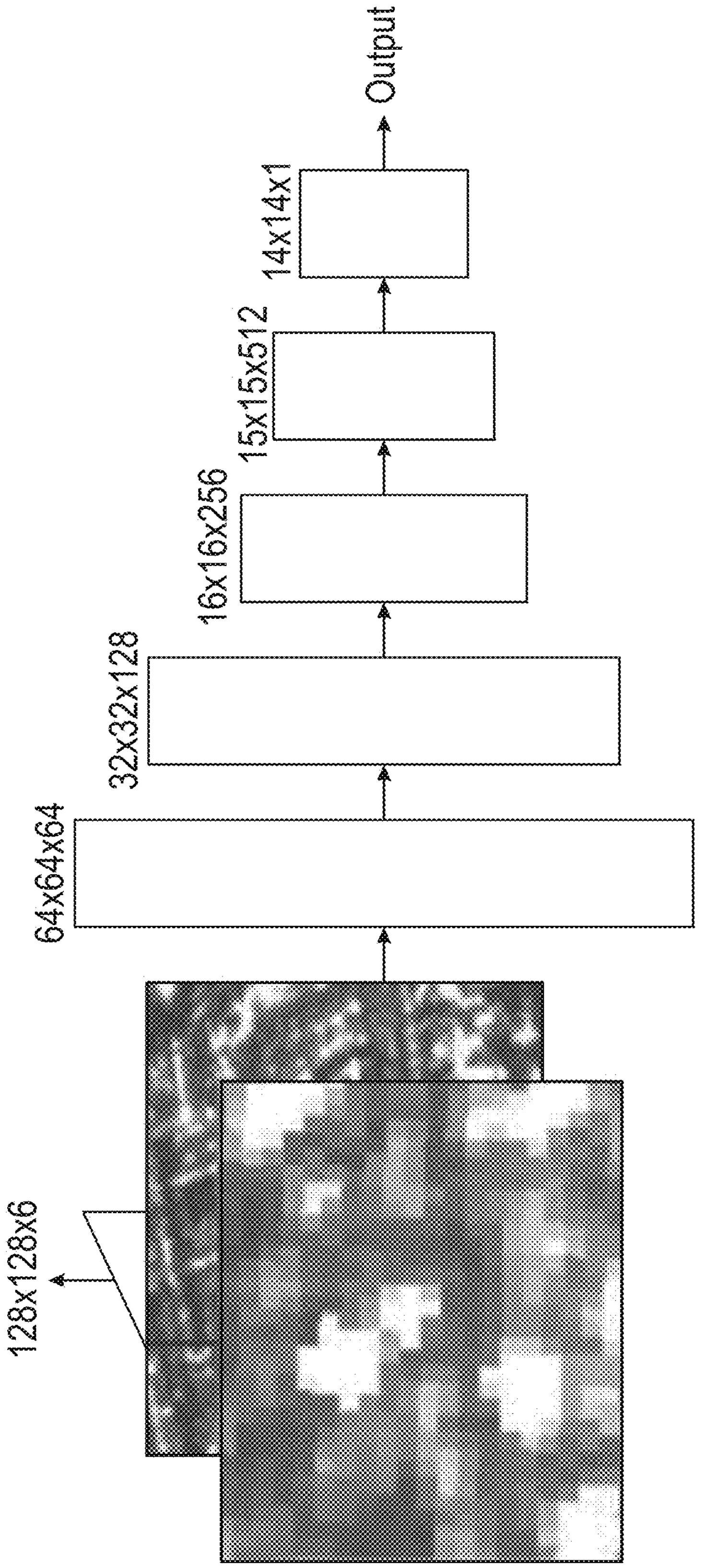
FIG. 5C illustrates an exemplary discriminator of a GAN model, in accordance with some embodiments.

FIG. 5B illustrates an exemplary generator 504 of a GAN model, in accordance with some embodiments. As shown, the generator 504 can employ a structure modified from the U-Net model with customized width and depth tuned on the data of interest. FIG. 5C illustrates an exemplary discriminator 510 of a GAN model, in accordance with some embodiments. As shown, the discriminator 510 can employ a structure modified from the discriminator of the PatchGAN model with customized width and depth tuned on the data of interest.

Figure 6:
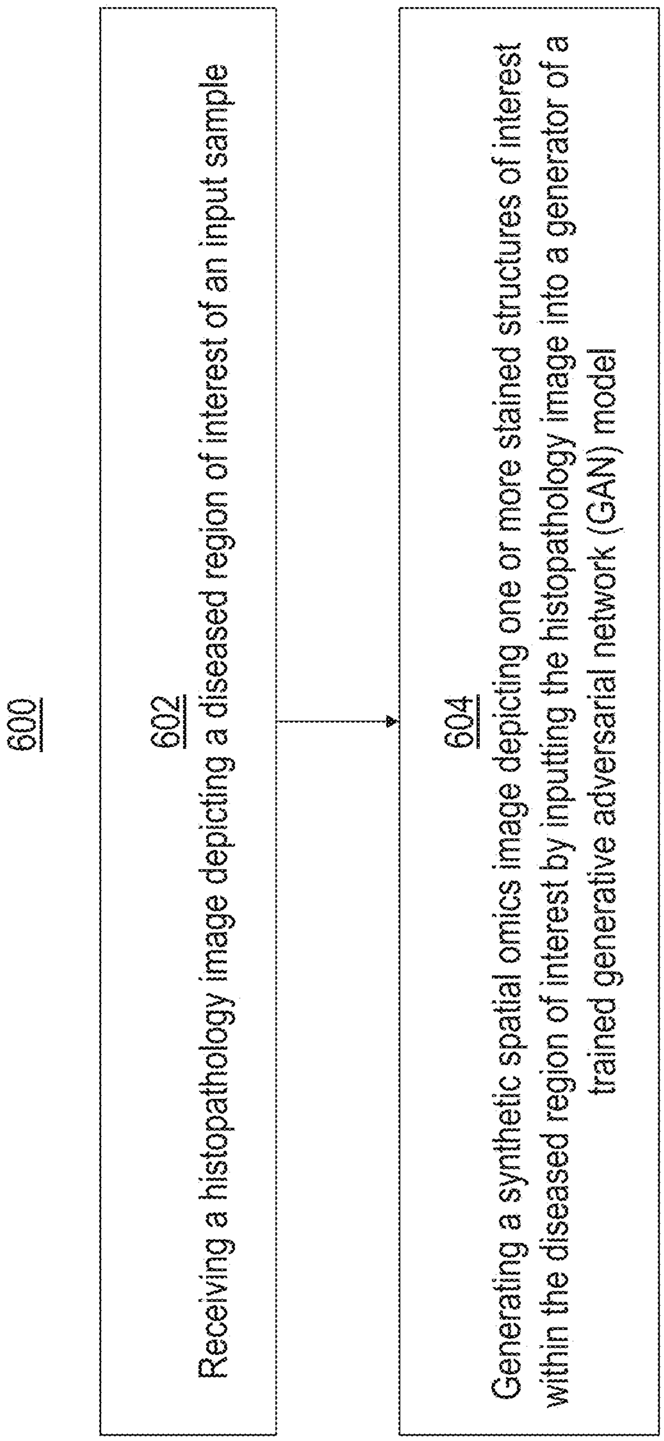
FIG. 6 illustrates an exemplary process for generating synthetic spatial omics images, according to some embodiments.

FIG. 6 illustrates an exemplary process 600 for generating synthetic spatial omics images, according to some embodiments. Process 600 is performed, for example, using one or more electronic devices implementing a software platform. In some examples, process 600 is performed using a client-server system, and the steps of process 600 are divided up in any manner between the server and one or more client devices. In other examples, process 600 is performed using only a client device or only multiple client devices. In process 600, some steps are, optionally, combined, the order of some steps is, optionally, changed, and some steps are, optionally, omitted. In some examples, additional steps may be performed in combination with the process 600. Accordingly, the operations as illustrated (and described in greater detail below) are exemplary by nature and, as such, should not be viewed as limiting.

Process 600 can be performed after a GAN model is trained in accordance with process 200. Once the GAN model is trained (e.g., using training data comprising both real histopathology image data and real spatial omics data) in accordance with process 200, it can be run in inference mode on histology datasets associated with a larger cohort. These datasets may be from the standard-of-care data, which comprises histopathology image data and outcome data of a larger cohort but do not include spatial omics data for the larger cohort. By process 600, the system can derive synthetic spatial omics data for the larger number of individuals. The synthetic spatial omics data can be used to power numerous downstream applications, as described herein.

At block 602, an exemplary system (e.g., one or more electronic devices) receives a histopathology image depicting a diseased region of interest of an input tissue sample. A histopathology image can include an image of a tissue sample (e.g., a biopsy or surgical specimen) that is processed and fixed onto glass slides. To visualize different components of the tissue sample, the tissue may be dyed using one or more stains. The histopathology image can provide insight into a disease and its effect on tissues because the preparation process preserves the morphological structures and characteristics of the tissue sample.

In some embodiments, the histopathology image comprises a hematoxylin and eosin (H&E) stain image, a trichrome stain image, an immuno-histochemistry (IHC) stain image using one or more antibodies, a Fluorescence In Situ Hybridization (FISH) stain image using one or more DNA or RNA probes. The histopathology image may be acquired in routine clinical care, as described herein.

At block 604, the system generates a synthetic spatial omics image depicting one or more stained structures of interest within the diseased region of interest. The synthetic spatial omics image mimics a real spatial omics image that provides information about biological molecules in their native location within a tissue sample to maintain the spatial context. In some embodiments, the synthetic spatial omics image comprises a synthetic spatial proteomics image, which can depict the spatially resolved abundance of expressed protein across the diseased region of interest. In some embodiments, the synthetic spatial omics image comprises a synthetic spatial transcriptomics image, which can depict the spatially resolved abundance of expressed RNA transcripts. In some embodiments, the synthetic spatial omics image comprises a synthetic spatial epigenetic image, which can depict the spatially resolved level of chromatin accessibility.

In some embodiments, the one or more stained structures of interest in the synthetic spatial omics image comprise one or more proteins of interest, DNA, and autofluorescence of tissues. In some embodiments, the one or more proteins of interest can comprise: DAPI, Cy5, TRITC, FOXP3 (D2W8E), Perforin_C, p-STAT3_C, HLA-I (A, B, or C), TGF-beta, GRZMB_A, GFAP_D, LAG-3_B, TMEM119_C, CD45RO_A, PD-1 EPR4877 (2), HLA-DR_B, PD-L1, CD68 PG-M1, CD19_A, NKG2D_B, TIM-3_A, CD20 L26, LCK_B, CD8 4B11, P2RY12_A, CD4 EPR6854, CD11c, CD205_D, CD163, CD31, or any combination thereof. The generator can be configured to generate image data across multiple channels corresponding to multiple structures of interest (e.g., multiple proteins).

To generate the synthetic spatial omics image, the system inputs the histopathology image received at block 302 into a generator of a trained generative adversarial network (GAN) model. The trained GAN model comprises a generator and a discriminator. The generator is configured to receive an input histopathology image and output a synthetic spatial omics image that is as close to a real spatial omics image corresponding to the input histopathology image as possible. The discriminator is configured to receive an input spatial omics image and output a classification of whether the input spatial omics image is real (e.g., sampled from real data) or synthetic (e.g., generated by the generator). By training both the generator and the discriminator iteratively, the generator can be trained to produces synthetic spatial omics images indistinguishable to real spatial omics images.

Generating synthetic spatial omics data in accordance with the techniques described herein provide numerous advantages. The synthetic spatial omics data is generated by simply inputting histopathology images into a trained GAN model. Accordingly, it can be significantly easier, cheaper, and faster to obtain than real spatial omics data, which require costly equipment and analytics and can be time-consuming. In contrast, the techniques described herein require less processing power and less energy, thus improving the functioning of a computer system.

Further, the GAN model can be trained using data of a smaller cohort (e.g., research cohort 102 in FIG. 1) and then be run in inference mode generate synthetic spatial omics data for a significantly larger cohort (e.g., cohort 112 in FIG. 1). The synthetic spatial omics data can be used in conjunction with other data readily available for the larger cohort (e.g., longitudinal outcome data, drug response data) to power downstream applications and discoveries.

In some embodiments, the system can use the synthetic spatial omics data of a cohort (e.g., obtained in block 604), along with other data available for the cohort, to train downstream machine learning models. For example, using synthetic spatial omics data and corresponding outcome data of the same subjects, the system can train a first downstream machine learning model (e.g., a supervised model) configured to receive a spatial omics image (real or synthetic) of an individual and predict an outcome for the individual. As another example, using synthetic spatial omics data and corresponding drug response data of the same subjects, the system can train a second downstream machine learning model (e.g., a supervised model) configured to receive a spatial omics image (real or synthetic) of an individual and predict a drug response for the individual.

In some embodiments, the system can input the synthetic spatial omics data of an individual (e.g., obtained in block 604) into one or more trained downstream machine learning models. For example, the system can input the synthetic spatial omics data of the individual (e.g., obtained in block 604) into a trained machine learning model configured to output a prediction of outcome for the individual, a prediction of drug response for the individual, etc.

In some embodiments, the system can use the synthetic spatial omics data of one or more individuals (e.g., obtained in block 604) to perform unsupervised learning to identify recurrent spatial motifs. In other words, based on the spatial omics data (e.g., where the cells are, what types of cells, what types of proteins are expressed), unsupervised learning can be performed to identify spatial patterns of interests or other biomarkers, which in turn may be predictive of patient outcome, drug response, etc.

In some embodiments, the synthetic spatial omics images can be used to provide a diagnosis. For example, the synthetic spatial omics data provides additional insight into the specimen such as how many immune cells there are, what type of immune cell they are (e.g., effector v. T-memory), protein expression (e.g., which are expressing PD-1, PD-L1, etc.). The diagnosis can be made by a human pathologist who can review the synthetic spatial omics images in conjunction with other data (e.g., histopathology images). For example, the system can display the synthetic spatial omics image data as an overlay over the histopathology image data. Additionally or alternatively, the diagnosis can be made automatically by a trained downstream machine learning model configured to receive spatial omics image data and output a diagnosis. The downstream machine learning model can be first trained using spatial omics image data (real or synthetic as obtained in block 604) and corresponding diagnosis data of a plurality of subjects.

In some embodiments, the synthetic spatial omics images can be used to identify a treatment (e.g., immunotherapy). For example, the synthetic spatial omics data provides additional insight into the specimen such as how many immune cells there are, what type of immune cell they are (e.g., effector v. T-memory), protein expression (e.g., which are expressing PD-1, PD-L1, etc.). The treatment can be determined by a human pathologist who can review the synthetic spatial omics images in conjunction with other data (e.g., histopathology images). For example, the system can display the synthetic spatial omics image data as an overlay over the histopathology image data. Additionally or alternatively, the diagnosis can be made automatically by a trained downstream machine learning model configured to receive spatial omics image data and output a recommended treatment. The downstream machine learning model can be first trained using spatial omics image data (real or synthetic as obtained in block 604) and corresponding treatment data of a plurality of subjects.

Figure 7:
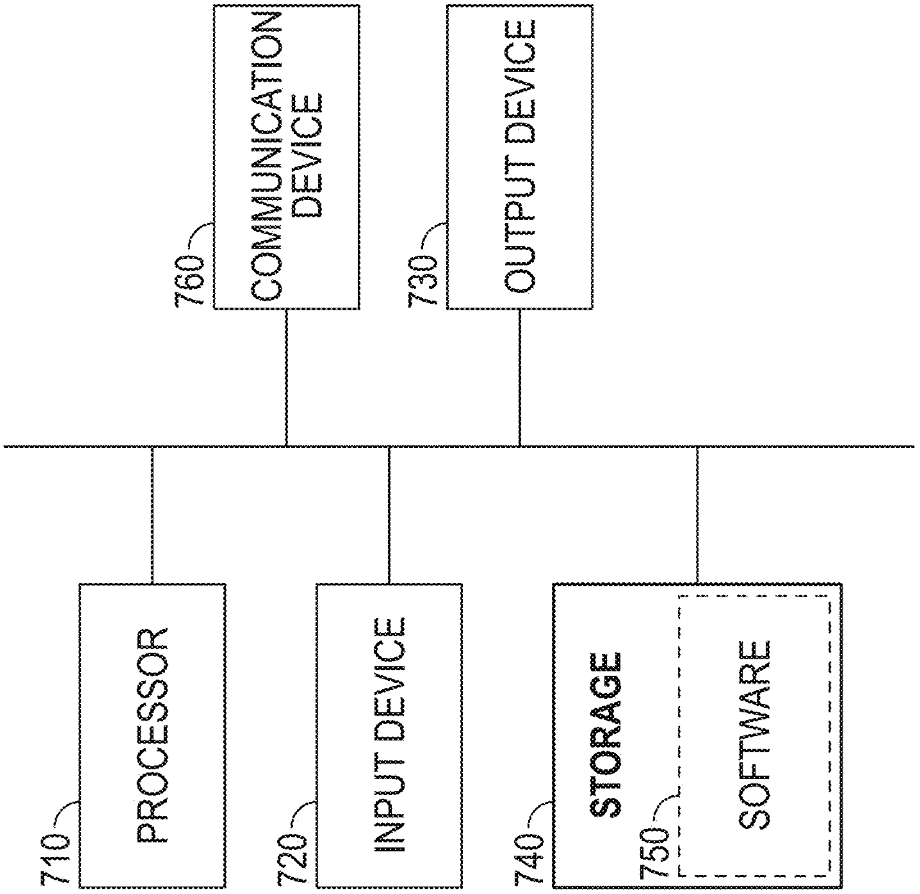
FIG. 7 illustrates an exemplary electronic device in accordance with some embodiments.

The operations described above are optionally implemented by components depicted in FIG. 7. It would be clear to a person having ordinary skill in the art how other processes are implemented based on the components depicted in FIG. 7.

FIG. 7 illustrates an example of a computing device in accordance with one embodiment. Device 700 can be a host computer connected to a network. Device 700 can be a client computer or a server. As shown in FIG. 7, device 700 can be any suitable type of microprocessor-based device, such as a personal computer, workstation, server or handheld computing device (portable electronic device) such as a phone or tablet. The device can include, for example, one or more of processor 710, input device 720, output device 730, storage 740, and communication device 760. Input device 720 and output device 730 can generally correspond to those described above, and can either be connectable or integrated with the computer.

Input device 720 can be any suitable device that provides input, such as a touch screen, keyboard or keypad, mouse, or voice-recognition device. Output device 730 can be any suitable device that provides output, such as a touch screen, haptics device, or speaker.

Storage 740 can be any suitable device that provides storage, such as an electrical, magnetic or optical memory including a RAM, cache, hard drive, or removable storage disk. Communication device 760 can include any suitable device capable of transmitting and receiving signals over a network, such as a network interface chip or device. The components of the computer can be connected in any suitable manner, such as via a physical bus or wirelessly.

Software 750, which can be stored in storage 740 and executed by processor 710, can include, for example, the programming that embodies the functionality of the present disclosure (e.g., as embodied in the devices as described above).

Software 750 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 740, that can contain or store programming for use by or in connection with an instruction execution system, apparatus, or device.

Software 750 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport readable medium can include, but is not limited to, an electronic, magnetic, optical, electromagnetic or infrared wired or wireless propagation medium.

Device 700 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Device 700 can implement any operating system suitable for operating on the network. Software 750 can be written in any suitable programming language, such as C, C++, Java or Python. In various embodiments, application software embodying the functionality of the present disclosure can be deployed in different configurations, such as in a client/server arrangement or through a Web browser as a Web-based application or Web service, for example.

Figure 8:
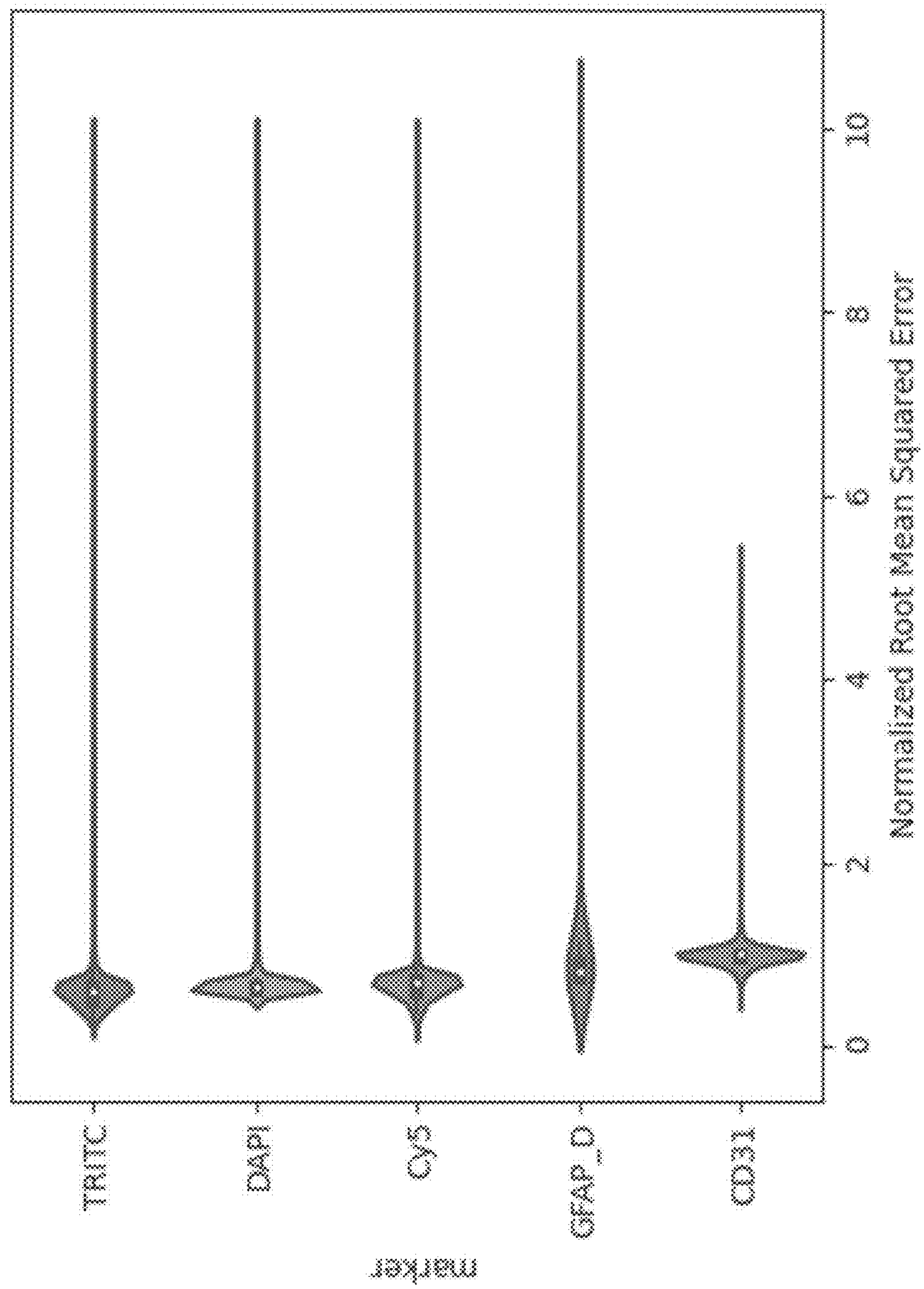
FIG. 8 illustrates exemplary quantitative measurements of performance of synthetic spatial omics images, in accordance with some embodiments.

FIG. 8 illustrates normalized root mean squared errors associated with exemplary synthetic spatial omics images generated using the techniques described herein, including synthetic TRITC images, synthetic DAPI images, synthetic Cy5 images, etc., in an exemplary implementation. As shown in FIG. 8, the techniques described herein can generate a variety of high-quality synthetic spatial omics images with relatively small deviation from real spatial omics images.

The foregoing description, for the purpose of explanation, has been described with reference to specific examples or aspects. However, the illustrative discussions above are not intended to be exhaustive or to limit the invention to the precise forms disclosed. For the purpose of clarity and a concise description, features are described herein as part of the same or separate variations; however, it will be appreciated that the scope of the disclosure includes variations having combinations of all or some of the features described. Many modifications and variations are possible in view of the above teachings. The variations were chosen and described in order to best explain the principles of the techniques and their practical applications. Others skilled in the art are thereby enabled to best utilize the techniques and various variations with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

What is claimed is:

1. A system for generating synthetic spatial omics images, comprising: one or more processors;

a memory; and one or more programs, wherein the one or more programs are stored in the memory and configured to be executed by the one or more processors, the one or more programs including instructions for:

receiving a histopathology image depicting a diseased region of interest of an input tissue sample; and generating a synthetic spatial omics image depicting one or more stained structures of interest within the diseased region of interest by inputting the histopathology image into a trained machine learning model, wherein the machine learning model is trained by:

receiving a training histopathology image of a training tissue sample, wherein the training histopathology image comprises a plurality of identified landmarks;

receiving a training spatial omics image of the training tissue sample, wherein the training spatial omics image comprises a plurality of identified landmarks;

registering the training histopathology image and the training spatial omics image based on the plurality of landmarks identified in the training histopathology image and the plurality of landmarks identified in the training spatial omics image;

generating, based on the registration of the training histopathology image and the training spatial omics image, a training dataset comprising a histopathology image set and a corresponding spatial omics image set; and training the machine learning model based on the generated training dataset.

2. The system of claim 1, wherein the histopathology image depicting the diseased region of interest of the input tissue sample comprises a hematoxylin and eosin (H&E) stain image, a trichrome stain image, an immuno-histochemistry (IHC) stain image, or a Fluorescence In Situ Hybridization (FISH) stain image.

3. The system of claim 1, wherein the generated synthetic spatial omics image comprises a synthetic spatial proteomics image, a synthetic spatial transcriptomics image, or a synthetic spatial epigenetic image.

4. The system of claim 1, wherein the one or more stained structures of interest comprise one or more proteins of interest, DNA, autofluorescence of tissues, or any combination thereof.

5. The system of claim 4, wherein the one or more proteins of interest comprise: DAPI, Cy5, TRITC, FOXP3 (D2W8E), Perforin_C, p-STAT3_C, HLA-I (A, B, or C), TGF-beta, GRZMB_A, GFAP_D, LAG-3_B, TMEM119_C, CD45RO_A, PD-1 EPR4877 (2), HLA-DR_B, PD-L1, CD68 PG-M1, CD19_A, NKG2D_B, TIM-3_A, CD20 L26, LCK_B, CD8 4B11, P2RY12_A, CD4 EPR6854, CD11c, CD205_D, CD163, CD31, or any combination thereof.

6. The system of claim 1, the one or more programs further including instructions for:

identifying the plurality of landmarks in the training histopathology image by isolating, from the training histopathology image, image data corresponding to the plurality of landmarks by performing color deconvolution.

7. The system of claim 1, the one or more programs further including instructions for:

identifying the plurality of landmarks in the training spatial omics image by isolating, from the training spatial omics image, image data corresponding to the plurality of landmarks by selecting a channel from a plurality of channels.

8. The system of claim 1, wherein the plurality of landmarks identified in the training histopathology image or the plurality of landmarks identified in the training spatial omics image comprise: one or more cell nuclei.

9. The system of claim 1, wherein registering the training histopathology image and the training spatial omics image comprising obtaining a transformation function.

10. The system of claim 1, the one or more programs further including instructions for: performing noise removal on the spatial omics image set of the training dataset.

11. The system of claim 1, wherein the machine learning model comprises a convolutional neural network.

12. The system of claim 11, wherein the machine learning model is based on a U-Net model.

13. The system of claim 1, the one or more programs further including instructions for: predicting, based on the synthetic spatial omics image, an outcome of a patient associated with the input tissue sample.

14. The system of claim 1, the one or more programs further including instructions for: identifying, based on the synthetic spatial comics image, a treatment for a patient associated with the input tissue sample.

15. The system of claim 1, the one or more programs further including instructions for: identifying, based on the synthetic spatial comics image, a biomarker.

16. The system of claim 1, the one or more programs further including instructions for: identifying, based on the synthetic spatial comics image, one or more spatial motifs.

17. The system of claim 1, the one or more programs further including instructions for: displaying the synthetic spatial omics image as an overlay over the histopathology image of the input tissue sample.

18. A method for generating synthetic spatial omics images, comprising: receiving a histopathology image depicting a diseased region of interest of an input tissue sample; and generating a synthetic spatial omics image depicting one or more stained structures of interest within the diseased region of interest by inputting the histopathology image into a trained machine learning model, wherein the machine learning model is trained by:

receiving a training histopathology image of a training tissue sample, wherein the training histopathology image comprises a plurality of identified landmarks;

receiving a training spatial omics image of the training tissue sample, wherein the training spatial omics image comprises a plurality of identified landmarks;

registering the training histopathology image and the training spatial omics image based on the plurality of landmarks identified in the training histopathology image and the plurality of landmarks identified in the training spatial omics image;

generating, based on the registration of the training histopathology image and the training spatial omics image, a training dataset comprising a histopathology image set and a corresponding spatial omics image set; and training the machine learning model based on the generated training dataset.

19. A non-transitory computer-readable storage medium storing one or more programs for generating synthetic spatial omics images, the one or more programs comprising instructions, which when executed by one or more processors of an electronic device, cause the electronic device to perform:

receiving a histopathology image depicting a diseased region of interest of an input tissue sample; and generating a synthetic spatial omics image depicting one or more stained structures of interest within the diseased region of interest by inputting the histopathology image into a trained machine learning model, wherein the machine learning model is trained by:

receiving a training histopathology image of a training tissue sample, wherein the training histopathology image comprises a plurality of identified landmarks;

receiving a training spatial omics image of the training tissue sample, wherein the training spatial omics image comprises a plurality of identified landmarks;

registering the training histopathology image and the training spatial omics image based on the plurality of landmarks identified in the training histopathology image and the plurality of landmarks identified in the training spatial omics image;

generating, based on the registration of the training histopathology image and the training spatial omics image, a training dataset comprising a histopathology image set and a corresponding spatial omics image set; and training the machine learning model based on the generated training dataset.

* * * * *